US012721752B2

(12) United States Patent
Park

(10) Patent No.: US 12,721,752 B2
(45) Date of Patent: Sep. 1, 2026

(54) SURGICAL TOOL AND SURGICAL TOOL SET FOR HANDLING VISCOELASTIC SUBSTANCE SYRINGE

(71) Applicant: Hyungju Park, Seoul (KR)

(72) Inventor: Hyungju Park, Seoul (KR)

( * ) Notice: Subject to any disclaimer, the term of this patent is extended or adjusted under 35 U.S.C. 154(b) by 21 days.

(21) Appl. No.: 19/083,728

(22) Filed: Mar. 19, 2025

(65) Prior Publication Data

US 2025/0213393 A1 Jul. 3, 2025

Related U.S. Application Data

(63) Continuation of application No. PCT/KR2024/006570, filed on May 14, 2024.

(30) Foreign Application Priority Data

Jun. 9, 2023 (KR) ........................ 10-2023-0073955

(51) Int. Cl.
*A61M 5/31* (2006.01)
*A61F 9/007* (2006.01)

(52) U.S. Cl.
CPC ................................ *A61F 9/00754* (2013.01)

(58) Field of Classification Search
CPC ............ A61M 5/3137; A61M 5/31501; A61M 5/31565; A61M 5/3271; A61M 5/3272; A61M 5/31585; A61M 5/3148; A61M 5/150259; A61M 5/150267; A61M 2005/3142; A61M 2005/31588; A61M 2005/3139
See application file for complete search history.

(56) References Cited

U.S. PATENT DOCUMENTS

| | | | | |
|---|---|---|---|---|
| 4,687,472 A * | 8/1987 | Gross | A61M 5/31 | 604/223 |
| 4,744,790 A * | 5/1988 | Jankowski | A61M 5/24 | 604/232 |
| 2003/0034264 A1 | 2/2003 | Hamai | | |
| 2006/0264825 A1* | 11/2006 | Westbye | A61M 5/326 | 604/110 |
| 2016/0089497 A1* | 3/2016 | Fojtik | A61M 5/3137 | 604/227 |
| 2016/0287805 A1 | 10/2016 | Holmqvist | | |
| 2024/0075212 A1* | 3/2024 | Peterson | A61M 5/3137 | |

FOREIGN PATENT DOCUMENTS

| | | |
|---|---|---|
| JP | 2003052819 A | 2/2003 |
| JP | 2003250889 A | 9/2003 |
| KR | 1020150121632 A | 10/2015 |

OTHER PUBLICATIONS

International Search Report of PCT/KR2024/006570 dated Aug. 20, 2024.

* cited by examiner

*Primary Examiner* — Tuan V Nguyen
(74) *Attorney, Agent, or Firm* — Dinsmore & Shohl LLP; Yongsok Choi, Esq.

(57) ABSTRACT

A surgical tool for handling a viscoelastic substance syringe includes a body configured to allow a syringe in which a viscoelastic substance is stored to be coupled to the body in a front-rear direction, a first gripping part protruding from the body in one side direction perpendicular to the front-rear direction, and a second gripping part protruding from the body in an opposite direction to the one side direction.

10 Claims, 7 Drawing Sheets

SURGICAL TOOL AND SURGICAL TOOL SET FOR HANDLING VISCOELASTIC SUBSTANCE SYRINGE

CROSS-REFERENCE TO RELATED APPLICATION

This application is a bypass continuation application of International Patent Application No. PCT/KR2024/006570 having an international filing date of May 14, 2024 and designating the United States, the international application being based upon and claiming the benefit of priority from Korean Patent Application No. 10-2023-0073955 filed on Jun. 9, 2023, the entire contents of which are incorporated herein by reference.

TECHNICAL FIELD

The present disclosure relates to a surgical tool and a surgical tool set for handling a viscoelastic substance syringe.

BACKGROUND

A transparent lens inside a human eye plays an important role in focusing on an object to provide clear vision. The transparent lens may become cloudy due to aging, eye inflammation, or trauma. Accordingly, a cataract, a type of ophthalmic disease, may develop. If a cataract progresses to the point of causing discomfort in daily life, surgery should be considered as medication does not improve symptoms.

Cataract surgery is performed in a manner of making a small hole in the black or white part of an eye, inserting an ultrasonic device into the hole to suction out a cataractous lens, and then inserting a permanent artificial lens in its place. Specifically, continuous curvilinear capsulorrhexis (CCC) is performed by making an incision in a cornea, injecting viscoelastics having a predetermined viscosity between the cornea and a lens, and making a circular incision in an anterior capsule located at the front of a lens capsule. In this process, the viscoelastics are injected between the cornea and the lens to form a predetermined space to facilitate an insertion of a surgical instrument, an artificial lens, or the like. Then, as the viscoelastics are injected through an incised opening of the anterior capsule, the cataractous lens is suctioned using ultrasound. In this process, the viscoelastics prevent the lens capsule from shrinking due to a lack of moisture caused by the incision of the anterior capsule of the lens, and serve to maintain the lens capsule in a certain shape. Thereafter, the artificial lens is inserted and attached to the lens capsule to be fixed. The viscoelastics may be suctioned and removed before and after the insertion of the artificial lens.

Generally, the viscoelastic substance is stored or filled in a syringe to be provided. An operator injects the viscoelastic substance using the syringe containing the viscoelastic substance. Since the viscoelastic substance has high viscosity in order to maintain the shape of the lens capsule, handling operations are needed to carry the viscoelastic substance during the procedure. For example, handling the viscoelastic substance is performed with a tool known as a chopper, which has a needle-like shape.

SUMMARY

However, conventionally, if handling of a viscoelastic substance is required while the viscoelastic substance is injected into a lens capsule, an injection tool for the viscoelastic substance is first retracted from the lens capsule, and then a handling tool for handling the viscoelastic substance is inserted into the lens capsule. In addition, after handling the viscoelastic substance, the handling tool is retracted, and the injection tool is inserted again. As such, repeated insertion and retraction of the injection tool and the handling tool may cause astigmatism. Furthermore, in case that the injection tool and the handling tool are repeatedly inserted and retracted, surgery time may be prolonged.

Embodiments of the present disclosure improve or solve at least some problems with a conventional insertion tool and handling tool for a viscoelastic substance. To this end, multiple embodiments provide a surgical tool for handling a viscoelastic substance syringe, which may perform both injection and handling of viscoelastic substances in a state in which the surgical tool is inserted.

Further, multiple embodiments provide a surgical tool set for handling a viscoelastic substance syringe, the surgical tool set including the surgical tool for handling a viscoelastic substance syringe.

Embodiments according to one aspect of the preset disclosure are directed to a surgical tool for handling a viscoelastic substance syringe. The surgical tool for handling a viscoelastic substance syringe according to an exemplary embodiment includes: a body configured to allow a syringe, in which a viscoelastic substance is stored, to be coupled to the body in a front-rear direction; a first gripping part protruding from the body in one side direction perpendicular to the front-rear direction; and a second gripping part protruding from the body in an opposite direction to the one side direction.

In one embodiment, the body may include: a front plate having a first through-hole through which the syringe penetrates in the front-rear direction; a rear plate having a second through-hole through which the syringe penetrates in the front-rear direction; a hollow part communicating the first through-hole with the second through-hole in the front-rear direction; a first side wall disposed in the one side direction with respect to the hollow part to connect the front plate and the rear plate, the first gripping part being fixed to the first side wall; and a second side wall disposed in the opposite direction with respect to the hollow part to connect the front plate and the rear plate, the second gripping part being fixed to the second side wall.

In one embodiment, the front plate and the rear plate may be arranged parallel to each other. The first side wall and the second side wall may be arranged parallel to each other.

In one embodiment, the hollow part may be open in a side direction perpendicular to the one side direction and the front-rear direction.

In one embodiment, the first gripping part may include: a first gripping ring having a first through-hole formed in a side direction perpendicular to the one side direction and the front-rear direction so as to allow finger insertion; a second gripping ring connected to a rear of the first gripping ring and having a second through-hole formed in the side direction so as to allow finger insertion; and a third gripping ring connected to a rear of the second gripping ring and having a third through-hole formed in the side direction so as to allow finger insertion.

In one embodiment, the third through-hole may be smaller than the first through-hole and the second through-hole.

In one embodiment, the second gripping part may include a fourth gripping ring having a fourth through-hole formed in the side direction so as to allow finger insertion. The fourth through-hole may be larger than the first through-hole, the second through-hole, and the third through-hole.

In one embodiment, the fourth gripping ring may include: a front extension part defining a front boundary of the fourth through-hole and having a flat front end surface and a flat rear end surface extending from the body in the opposite direction; and a rear extension part defining a rear boundary of the fourth through-hole and having a flat front end surface and a flat rear end surface extending from the body in the opposite direction.

In one embodiment, the body, the first gripping part, and the second gripping part may be integrally formed.

Embodiments according to another aspect of the preset disclosure are directed to a surgical tool set for handling a viscoelastic substance syringe. The surgical tool set for handling a viscoelastic substance syringe according to an exemplary embodiment includes: a syringe in which a viscoelastic substance is stored; a body including a front plate having a first through-hole through which the syringe penetrates in a front-rear direction and which is formed at a front end, and a rear plate having a second through-hole through which the syringe penetrates in a front-rear direction and which is formed at a rear end and spaced apart from the front plate; a first gripping part protruding from the body in one side direction perpendicular to the front-rear direction; and a second gripping part protruding from the body in an opposite direction to the one side direction.

In one embodiment, the syringe may include at least one flange protruding from a rear end of the syringe in an outer radial direction. A front end surface of the flange may be engaged with a rear end surface of the rear plate in a state where the syringe penetrates through the first through-hole and the second through-hole.

According to the surgical tool for handling a viscoelastic substance syringe according to various embodiments of the present disclosure, the syringe is coupled to the body and a first gripping part and a second gripping part protrude in opposite directions of the body, so that an operator can inject and handle the viscoelastic substance while maintaining at least a portion of the syringe, which is coupled to the surgical tool, within the lens capsule. Therefore, since there is no need to alternately insert and retract different tools for injecting and handling the viscoelastic substance, astigmatism can be prevented or suppressed. Furthermore, the time required for surgery can be reduced.

DETAILED DESCRIPTION

Figure 1:
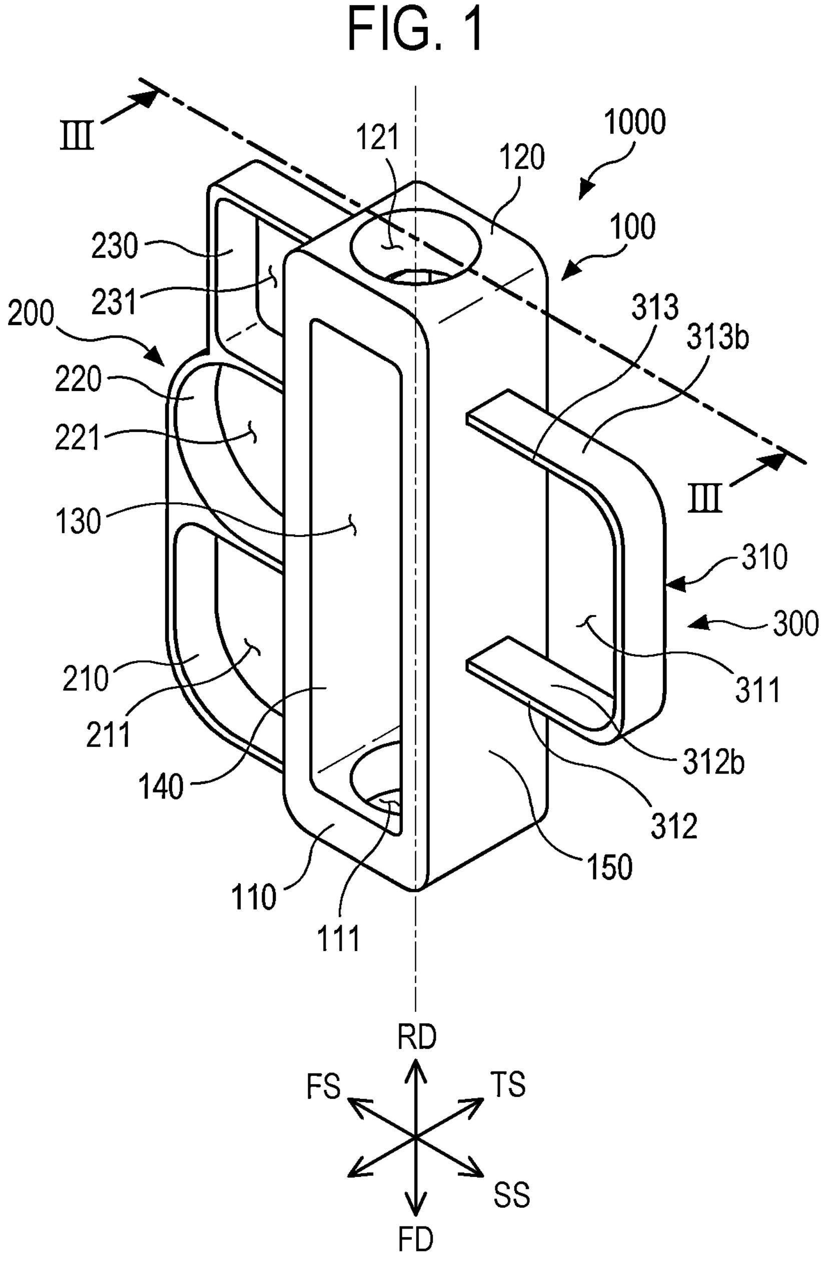
FIG. 1 is a perspective view illustrating a surgical tool for handling a viscoelastic substance syringe according to one embodiment of the present disclosure.

Embodiments of the present disclosure are illustrated for the purpose of explaining the technical idea of the present disclosure. The scope of the rights according to the present disclosure is not limited to the embodiments presented below or the detailed descriptions of such embodiments.

All technical terms and scientific terms used in the present disclosure include meanings that are commonly understood by a person of ordinary skill in the art to which the present disclosure belongs unless otherwise defined. All of the terms used in the present disclosure are selected for the purpose of describing the present disclosure more clearly, and are not selected to limit the scope of rights according to the present disclosure.

As used in the present disclosure, expressions such as "including," "comprising," "having," and the like are to be understood as open-ended terms having the possibility of encompassing other embodiments, unless otherwise mentioned in the phrase or sentence containing such expressions.

The singular expressions that are described in the present disclosure may encompass plural expressions unless otherwise stated, which will be also applied to the singular expressions recited in the claims.

The expressions "first," "second," and the like used in the present disclosure, are intended to distinguish between multiple elements, and are not intended to limit the sequence or importance of the corresponding elements.

In the present disclosure, where it is mentioned that one element is "connected" or "coupled" to another element, it is to be understood that said one element may be directly connected or coupled to said another element, or may be connected or coupled to said another element via a new additional element.

The directional terms such as "front" and "forward (FD)" used in the present disclosure are based on the direction in which the first gripping ring is positioned relative to the second gripping ring in the accompanying drawings, while terms like "back" and "rearward (RD)" refer to the opposite direction. The first and second gripping rings shown in the accompanying drawings may be oriented differently, and these directional terms may be interpreted accordingly.

Hereinafter, embodiments of the present disclosure will be described with reference to the accompanying drawings. Throughout the accompanying drawings, identical or corresponding elements are given the same reference numerals. Furthermore, repeated description of the same or corresponding components may be omitted in the following description of embodiments. However, omission of a description of components is not intended to mean exclusion of the components from the embodiments.

FIG. 1 is a perspective view illustrating a surgical tool for handling a viscoelastic substance syringe according to one embodiment of the present disclosure.

As shown in FIG. 1, the surgical tool 1000 for handling the viscoelastic substance syringe (hereinafter, simply referred to as "surgical tool") includes a body 100, a first gripping part 200, and a second gripping part 300. The body 100 is configured to have a syringe 400 (see FIGS. 4 to 7 described below), in which a viscoelastic substance is stored or filled, coupled thereto in a front-rear direction (FD-RD). For example, the syringe 400 may be coupled to the body 100 in a direction from the rear (RD) of the body 100 to the front (FD) of the body 100. The first gripping part 200 protrudes from the body 100 in a first side direction (FS) which is one side direction perpendicular to the front-rear direction (FD-RD). The second gripping part 300 protrudes from the body 100 in a second side direction (SS) opposite to the one side direction.

As described above, the syringe 400 is coupled to the body 100. The first gripping part 200 and the second gripping part 300 protrude in opposite directions (i.e., the first side direction (FS) and the second side direction (SS)). Thus, an operator can inject and handle the viscoelastic substance while maintaining at least a portion of the syringe 400, which is coupled to the surgical tool 1000, within the lens capsule. Therefore, since there is no need to alternately insert and retract different tools for injecting and handling the viscoelastic substance, astigmatism can be prevented or suppressed. Furthermore, the time required for surgery can be reduced.

In one embodiment, the body 100, the first gripping part 200, and the second gripping part 300 may be integrally configured. For example, the body 100, the first gripping part 200, and the second gripping part 300 may be made of the same metal material. In addition, the body 100, the first gripping part 200, and the second gripping part 300 may be manufactured through casting or die casting to have a shape according to various embodiments described below.

Figure 2:
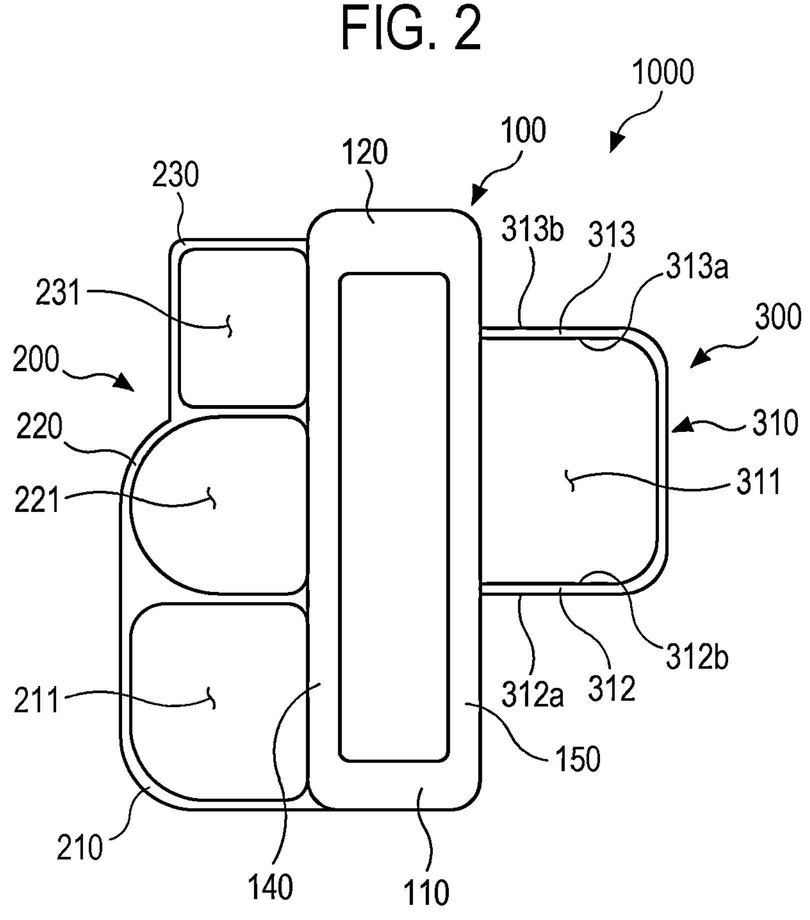
FIG. 2 is a front view illustrating the surgical tool for handling the viscoelastic substance syringe shown in FIG. 1.
Figure 3:
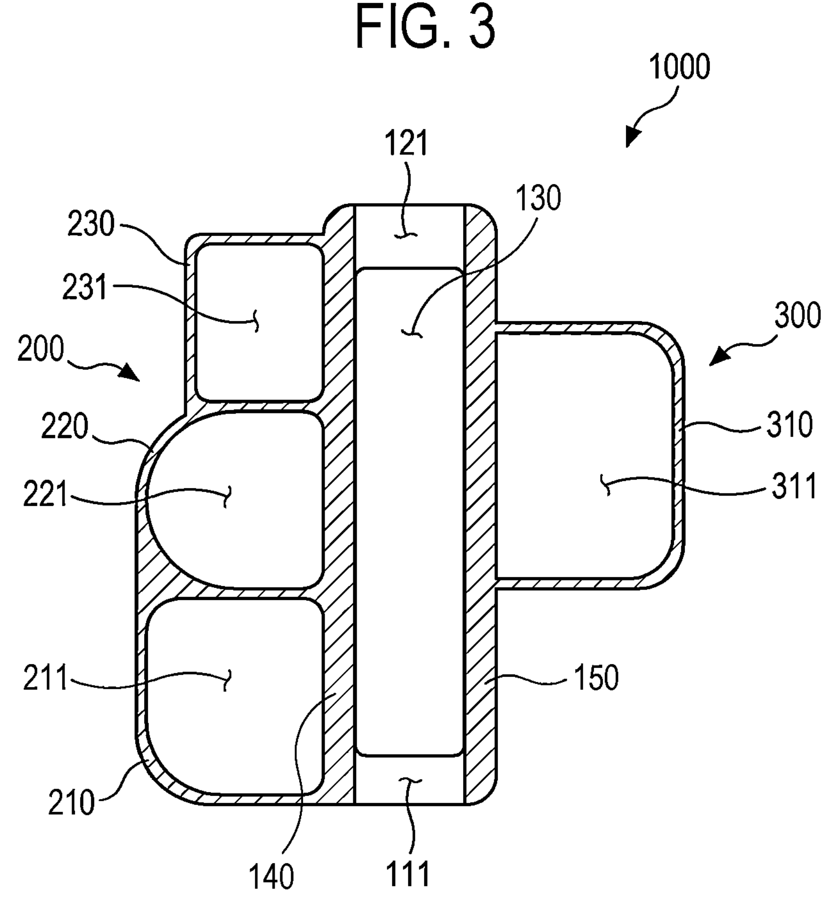
FIG. 3 is a cross-sectional view taken along the line III-III shown in FIG. 1.

FIG. 2 is a front view illustrating the surgical tool for handling a viscoelastic substance syringe shown in FIG. 1. FIG. 3 is a cross-sectional view taken along line III-III shown in FIG. 1.

In one embodiment, as shown in FIGS. 2 and 3, the body 100 may include a front plate 110, a rear plate 120, a hollow part 130, a first side wall 140, and a second side wall 150.

A first through-hole 111 through which the syringe 400 penetrates in the front-rear direction (FD-RD) is formed in the front plate 110. As one example, an inner diameter of the first through-hole 111 may have a size corresponding to an outer diameter of a barrel 410 of the syringe 400. Accordingly, in a state where the syringe 400 is mounted to the surgical tool 1000, since movement of the syringe 400 relative to the surgical tool 1000 is prevented, the operator can perform precise surgery.

A second through-hole 121 through which the syringe 400 penetrates in the front-rear direction (FD-RD) is formed in the rear plate 120. The rear plate 120 may be formed to be thicker than the front plate 110. In one embodiment, the front plate 110 and the rear plate 120 may be arranged parallel to each other. An inner diameter of the second through-hole 121 may have a size corresponding to the outer diameter of the barrel 410 of the syringe 400. In addition, since the barrel 410 of the syringe 400 generally has the same outer diameter along the front-rear direction (FD-RD), the inner diameter of the second through-hole 121 may be configured to be the same as the inner diameter of the first through-hole 111. Accordingly, in a state where the syringe 400 is mounted to the surgical tool 1000, since movement of the syringe 400 relative to the surgical tool 1000 is prevented, the operator may perform precise surgery.

The hollow part 130 communicates the first through-hole 111 with the second through-hole 121. In one embodiment, the hollow part 130 is open in a third side direction (TS) perpendicular to the first side direction (FS) and the second side direction (SS). For example, the hollow part 130 may be defined by configuring the first side wall 140 and the second side wall 150 to remain unconnected in the first side direction (FS) or the second side direction (SS). That is, an empty space defined between the first side wall 140 and the second side wall 150 may be understood as the hollow part 130. In a state where the syringe 400 is coupled to the surgical tool 1000, the barrel 410 of the syringe 400 may be located in the hollow part 130. Accordingly, while a viscoelastic substance is injected in a state where the syringe 400 is coupled to the surgical tool 1000, the operator can visually identify the remaining amount of the viscoelastic substance filled or stored in the barrel 410 through the hollow part 130. Further, by forming the hollow part 130, the overall weight of the surgical tool 1000 can be reduced. As a result, the operator's fatigue can be reduced.

The first side wall 140 is disposed in the first side direction (FS), which is one side direction with respect to the hollow part 130, to connect the front plate 110 and the rear plate 120 in the front-rear direction (FD-RD). The first gripping part 200 is fixed to the first side wall 140. A corner at which the first side wall 140 and the front plate 110 meet and a corner at which the first side wall 140 and the rear plate 120 meet may have a round shape. The first side wall 140 may have a thickness smaller than those of the front plate 110 and the rear plate 120.

The second side wall 150 is disposed in the second side direction (SS), which is an opposite direction of the one side direction with respect to the hollow part 130, to connect the front plate 110 and the rear plate 120 in the front-rear direction (FD-RD). The second gripping part 300 is fixed to the second side wall 150. A corner at which the second side wall 150 and the front plate 110 meet and a corner at which the second side wall 150 and the rear plate 120 meet may have a round shape. The second side wall 150 may have a thickness smaller than those of the front plate 110 and the rear plate 120. In one embodiment, the first side wall 140 and the second side wall 150 may be arranged parallel to each other.

In one embodiment, the front plate 110, the first side wall 140, the rear plate 120, and the second side wall 150 may configure an approximate rectangular shape connected to each other in a clockwise direction when viewed from the front with respect to the third side direction (TS).

In one embodiment, the first gripping part 200 may include a first gripping ring 210, a second gripping ring 220, and a third gripping ring 230. As one example, the first gripping ring 210, the second gripping ring 220, and the third gripping ring 230 may be sequentially configured from the front direction (FD) toward the rear direction (RD).

The first gripping ring 210 includes a first through-hole 211 formed in the third side direction (TS) perpendicular to the first side direction (FS) and the front-rear direction (FD-RD) to allow finger insertion. For example, a ring finger 40 may be inserted through the first through-hole 211. When viewed from the front with respect to the third side direction (TS), the first gripping ring 210 may have an approximate "ㄷ"-shape, and the first through-hole 211 may have an approximate "ㄷ"-shape to correspond to the shape of the first gripping ring 210.

The second gripping ring 220 is connected to a rear of the first gripping ring 210 and includes a second through-hole 221 formed in the third side direction (TS) to allow finger insertion. For example, a middle finger 30 may be inserted through the second through-hole 221. When viewed from the front, the second gripping ring 220 may have an approximate "C"-shape, and the second through-hole 221 may have a "C"-shape to correspond to the shape of the second gripping ring 220. In one embodiment, the second through-hole 221 may be formed to have a size approximately identical to that of the first through-hole 211.

The third gripping ring 230 is connected to a rear of the second gripping ring 220 and includes a third through-hole 231 formed in the third side direction (TS) to allow finger insertion. For example, an index finger 20 may be inserted through the third through-hole 231. When viewed from the front, the third gripping ring 230 may have an approximate "ㄷ"-shape, and the third through-hole 231 may have an approximate "ㄷ"-shape to correspond to the shape of the third gripping ring 230. In one embodiment, the third through-hole 231 may be formed to be smaller than the first through-hole 211 and the second through-hole 221.

In one embodiment, the second gripping part 300 may include a fourth gripping ring 310 including a fourth through-hole 311 formed in the third side direction (TS) to allow finger insertion. For example, a thumb 10 may be inserted through the fourth through-hole 311. When viewed from the front, the fourth gripping ring 310 may have an approximate "ㄷ"-shape with the left and right sides reversed. The fourth through-hole 311 may have an approximate "ㄷ"-shape with the left and right sides reversed to correspond to the shape of the fourth gripping ring 310. In one embodiment, the fourth through-hole 311 may be formed to be larger than the first through-hole 211, the second through-hole 221, and the third through-hole 231.

In one embodiment, the fourth gripping ring 310 may include a front extension part 312 and a rear extension part 313. The front extension part 312 defines a front boundary of the fourth through-hole 311. The front extension part 312 has a flat front end surface **312*a* and a flat rear end surface 312*b* extending from the body 100 in the second side direction (SS). The rear extension part 313 defines a rear boundary of the fourth through-hole 311. The rear extension part 313 has a flat front end surface 313*a* and a flat rear end surface 313*b* extending from the body 100 in the second side direction (SS). In case that the thumb 10 is inserted through the fourth through-hole 311 in order to inject the viscoelastic substance (see FIG. 7), the front extension part 312 and the rear extension part 313 support the inserted thumb 10 so as to prevent it from moving forward (FD) or backward (RD) with respect to the surgical tool 1000. In case that a little finger 50 is located at the front of the fourth gripping ring 310 to handle the viscoelastic substance (see FIG. 6), the little finger 50 comes in contact with the front extension part 312 to be supported by the front extension part 312**.

Figure 4:
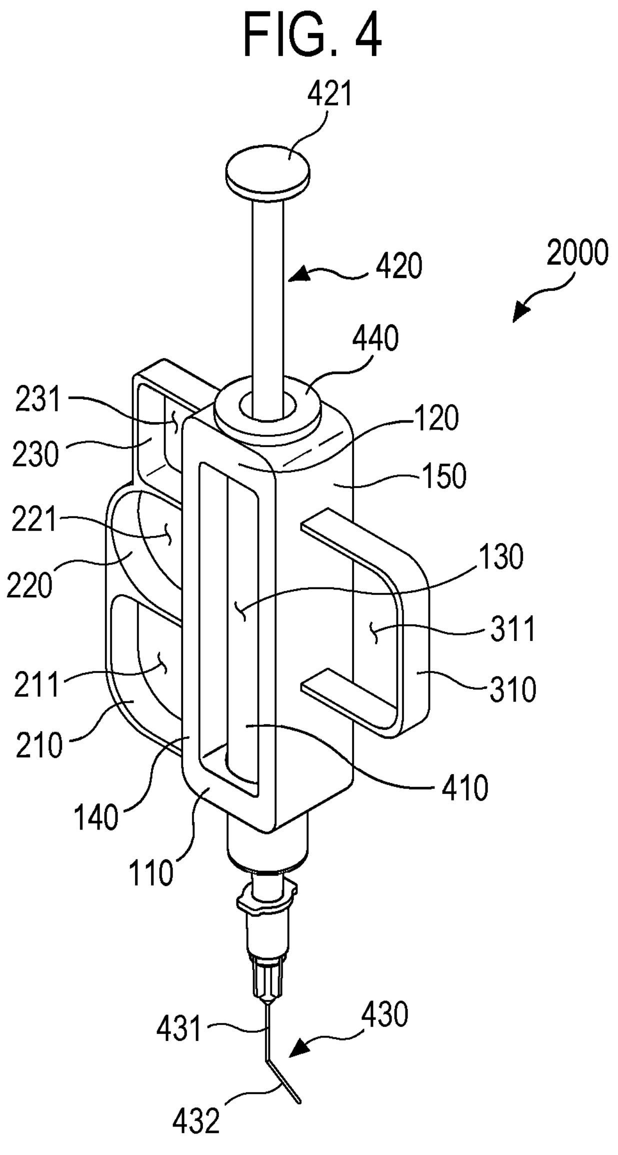
FIG. 4 is a perspective view illustrating a surgical tool set for handling a viscoelastic substance syringe according to one embodiment of the present disclosure.
Figure 5:
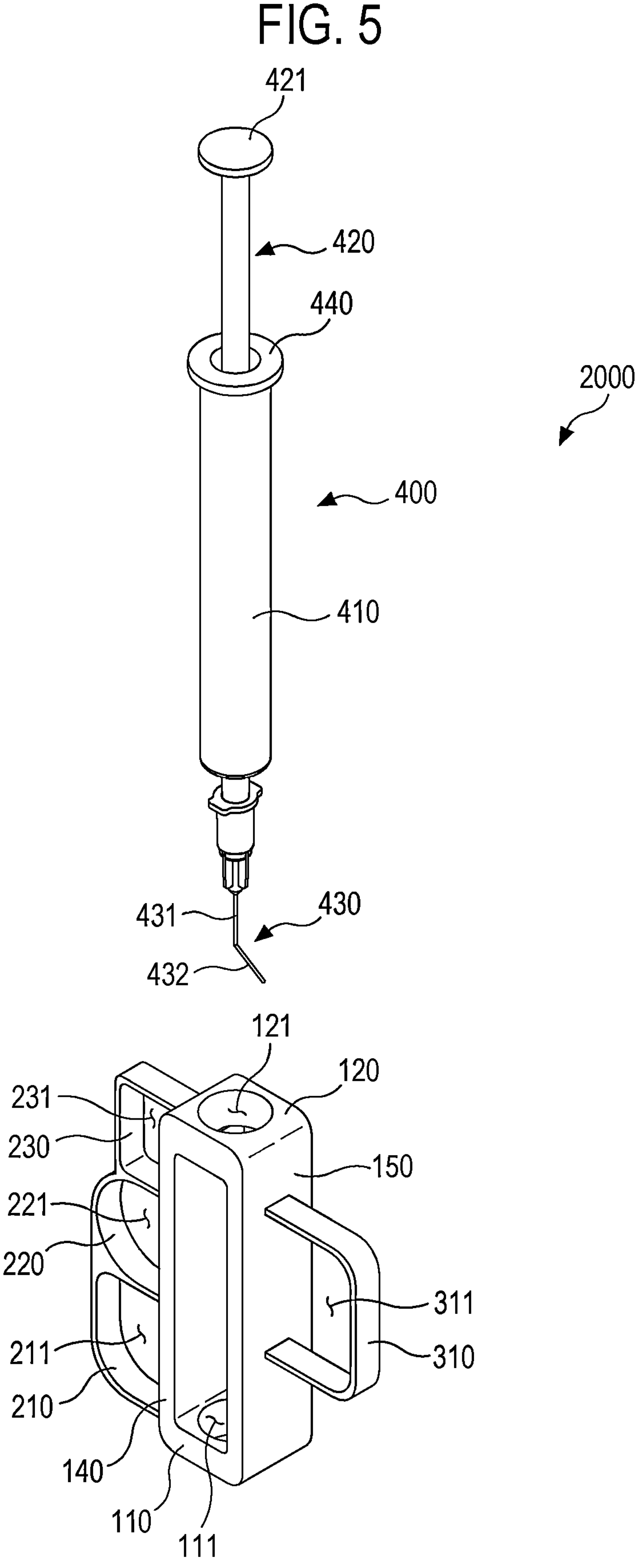
FIG. 5 is an exploded perspective view illustrating the surgical tool set for handling the viscoelastic substance syringe shown in FIG. 4.

FIG. 4 is a perspective view illustrating a surgical tool set for handling a viscoelastic substance syringe according to one embodiment of the present disclosure. FIG. 5 is an exploded perspective view illustrating the surgical tool set for handling the viscoelastic substance syringe shown in FIG. 4.

As shown in FIGS. 4 and 5, as another aspect of the present disclosure, the surgical tool set 2000 for handling the viscoelastic substance syringe (hereinafter, simply referred to as "surgical tool set") includes a syringe 400, a body 100, a first gripping part 200, and a second gripping part 300. Since the body 100, the first gripping part 200, and the second gripping part 300 according to this embodiment are the same as or similar to the body 100, the first gripping part 200, and the second gripping part 300 according to the embodiments shown in FIGS. 1 to 3, a detailed description of these components will be omitted, and the description will focus on the syringe 400 and components related thereto.

A viscoelastic substance is stored or filled in the syringe 400. The syringe 400 is coupled to the body 100 of the surgical tool 1000 by sequentially penetrating through the second through-hole 121 of the rear plate 120 and the first through-hole 111 of the front plate 110 from the rear (RD) toward the front (FD). For example, the syringe 400 may include a barrel 410 in which the viscoelastic substance is filled or stored, a plunger 420 configured to pressurize the viscoelastic substance, and a needle 430 through which the viscoelastic substance is discharged. A thumb pressure bar 421 is disposed at the rear end of the plunger 420. The needle 430 includes a first extension part 431 having a pipe shape extending in the front-rear direction (FD-RD) and a second extension part 432 having a pipe shape bent at a predetermined angle from the first extension part 431. The viscoelastic substance is discharged through a front end of the second extension part 432 by forward movement of the plunger 420 to be injected into the lens capsule.

In one embodiment, the syringe 400 may include at least one flange 440 protruding from the rear end thereof in an outer radial direction. The flange 440 is disposed at the rear end of the barrel 410. In the embodiments shown in FIGS. 4 and 5, although it is described that the flange 440 is disposed at the rear end of the barrel 410 along a circumferential direction to have a ring shape, two or more flanges may be disposed to be spaced apart from each other at equal intervals along the circumferential direction. The flange 440 according to one embodiment may be understood as a finger support of a typical syringe or a finger flange. In this embodiment, in a state where the barrel 410 of the syringe 400 penetrates through the first through-hole 111 and the second through-hole 121, a front end surface of the flange 440 is configured to be engaged with a rear end surface of the rear plate 120. Accordingly, the operator may inject or handle the viscoelastic substance by gripping the first gripping part 200 and the second gripping part 300 instead of gripping the flange 440 with fingers.

Figure 6:
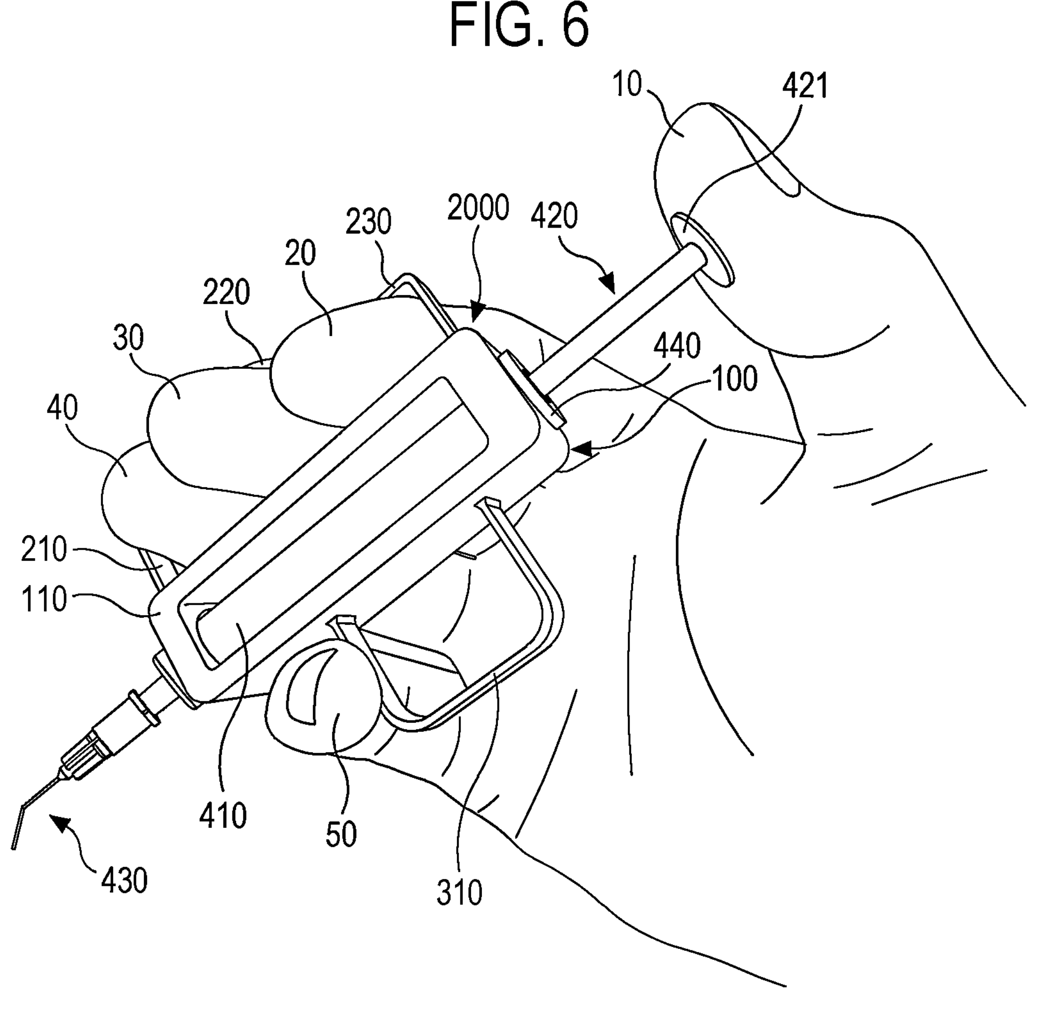
FIG. 6 is a perspective view schematically illustrating a first use example of the surgical tool set for handling the viscoelastic substance syringe shown in FIG. 4.

FIG. 6 is a perspective view schematically illustrating a first use example of the surgical tool set for handling the viscoelastic substance syringe shown in FIG. 4.

As shown in FIG. 6, in order to inject the viscoelastic substance, the operator may grip the surgical tool set 2000 by inserting the ring finger 40 into the first through-hole 211 of the first gripping ring 210, inserting the middle finger 30 into the second through-hole 221 of the second gripping ring 220, inserting the index finger 20 into the third through-hole 231 of the third gripping ring 230, positioning the little finger 50 onto the front end surface **312*a* of the front extension part 312 of the fourth gripping ring 310, and positioning the thumb 10 onto the thumb pressure bar 421 of the plunger 420. In this state, the operator can inject the viscoelastic substance by pressing the thumb pressure bar 421 of the plunger 420 forward (FD) with the thumb 10**.

Figure 7:
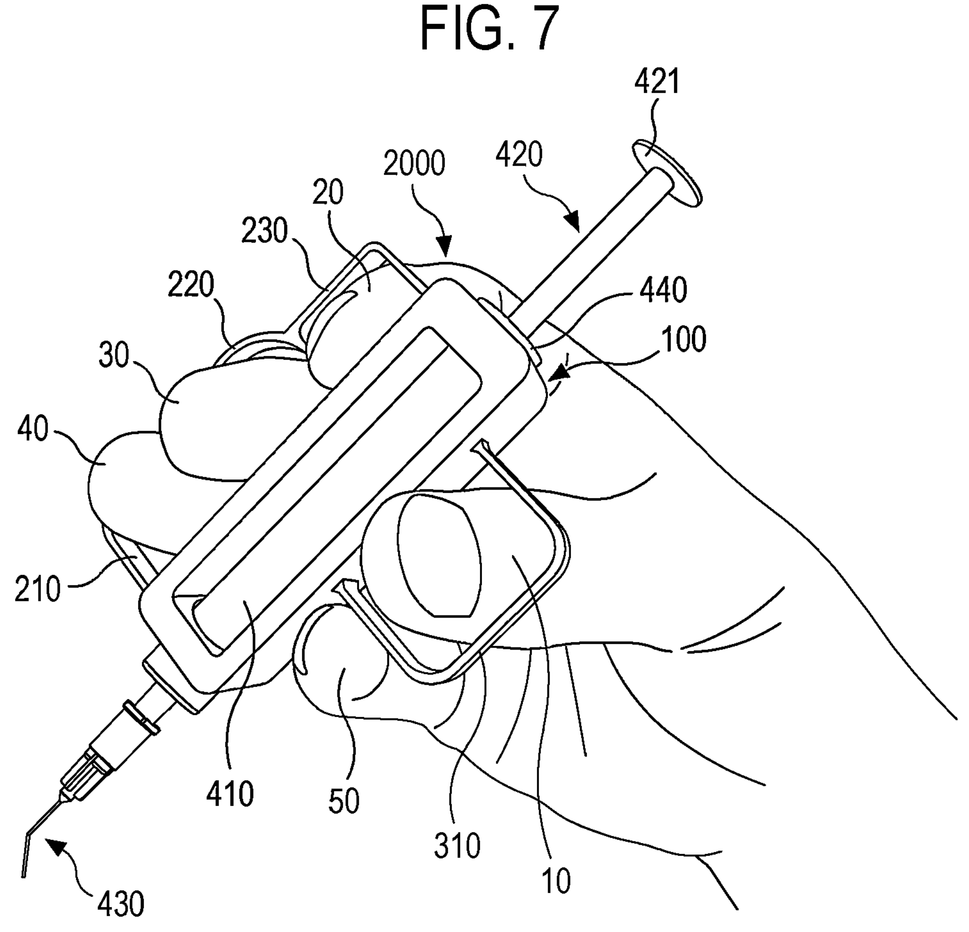
FIG. 7 is a perspective view schematically illustrating a second use example of the surgical tool set for handling the viscoelastic substance syringe shown in FIG. 4.

FIG. 7 is a perspective view schematically illustrating a second use example of the surgical tool set for handling the viscoelastic substance syringe shown in FIG. 4.

As shown in FIG. 7, in order to handle a viscoelastic substance, the operator may grip the surgical tool set 2000 by inserting the thumb 10 into the fourth through-hole 311 of the fourth gripping ring 310 while maintaining the ring finger 40, the middle finger 30, the index finger 20, and the little finger 50 in the state shown in FIG. 6. In this state, the operator can handle the viscoelastic substance. As another use example in the handling of the viscoelastic substance, the operator may handle the viscoelastic substance in a state of separating the little finger 50 from the front extension part 312 of the fourth gripping ring 310 while maintaining the ring finger 40, the middle finger 30, the index finger 20, and the thumb 10 in the state shown in FIG. 7. As such, by changing a position of the thumb 10, switching between injection and handling of the viscoelastic substance is possible. As a result, time required for surgery can be reduced.

The technical idea of the present disclosure has been described heretofore with reference to some embodiments and examples shown in the accompanying drawings. However, it is to be understood that various substitutions, modifications and alterations may be made without departing from the technical idea and scope of the present disclosure that can be understood by those of ordinary skill in the technical field to which the present disclosure pertains. Further, it is to be understood that such substitutions, modifications and alterations fall within the scope of the appended claims.

What is claimed is:

1. A surgical tool for handling a viscoelastic substance syringe, the surgical tool comprising:

a body configured to allow a syringe, in which a viscoelastic substance is stored, to be coupled to the body in a front-rear direction;

a first gripping part protruding from the body in one side direction perpendicular to the front-rear direction; and a second gripping part protruding from the body in an opposite direction to the one side direction;

wherein the first gripping part includes:

a first gripping ring having a first through-hole formed in a side direction perpendicular to the one side direction and the front-rear direction so as to allow finger insertion;

a second gripping ring connected to a rear of the first gripping ring and having a second through-hole formed in the side direction so as to allow finger insertion; and a third gripping ring connected to a rear of the second gripping ring and having a third through-hole formed in the side direction so as to allow finger insertion.

2. The surgical tool of claim 1, wherein the body includes:

a front plate having a first through-hole through which the syringe penetrates in the front-rear direction;

a rear plate having a second through-hole through which the syringe penetrates in the front-rear direction;

a hollow part communicating the first through-hole with the second through-hole in the front-rear direction;

a first side wall disposed in the one side direction with respect to the hollow part to connect the front plate and the rear plate, the first gripping part being fixed to the first side wall; and a second side wall disposed in the opposite direction with respect to the hollow part to connect the front plate and the rear plate, the second gripping part being fixed to the second side wall.

3. The surgical tool of claim 2, wherein the front plate and the rear plate are arranged parallel to each other, and wherein the first side wall and the second side wall are arranged parallel to each other.

4. The surgical tool of claim 2, wherein the hollow part is open in a side direction perpendicular to the one side direction and the front-rear direction.

5. The surgical tool of claim 1, wherein the third through-hole is smaller than the first through-hole and the second through-hole.

6. The surgical tool of claim 1, wherein the second gripping part includes a fourth gripping ring having a fourth through-hole formed in the side direction so as to allow finger insertion, and wherein the fourth through-hole is larger than the first through-hole, the second through-hole, and the third through-hole.

7. The surgical tool of claim 6, wherein the fourth gripping ring includes:

a front extension part defining a front boundary of the fourth through-hole and having a flat front end surface and a flat rear end surface extending from the body in the opposite direction; and a rear extension part defining a rear boundary of the fourth through-hole and having a flat front end surface and a flat rear end surface extending from the body in the opposite direction.

8. The surgical tool of claim 1, wherein the body, the first gripping part, and the second gripping part are integrally formed.

9. A surgical tool set for handling a viscoelastic substance syringe, the surgical tool set comprising:

a syringe in which a viscoelastic substance is stored;

a body including a front plate having a first through-hole through which the syringe penetrates in a front-rear direction and which is formed at a front end, and a rear plate having a second through-hole through which the syringe penetrates in a front-rear direction and which is formed at a rear end and spaced apart from the front plate;

a first gripping part protruding from the body in one side direction perpendicular to the front-rear direction; and a second gripping part protruding from the body in an opposite direction to the one side direction;

wherein the first gripping part includes:

a first gripping ring having a first through-hole formed in a side direction perpendicular to the one side direction and the front-rear direction so as to allow finger insertion;

a second gripping ring connected to a rear of the first gripping ring and having a second through-hole formed in the side direction so as to allow finger insertion; and a third gripping ring connected to a rear of the second gripping ring and having a third through-hole formed in the side direction so as to allow finger insertion.

10. The surgical tool set of claim 9, wherein the syringe includes at least one flange protruding from a rear end of the syringe in an outer radial direction, and wherein a front end surface of the flange is engaged with a rear end surface of the rear plate in a state where the syringe penetrates through the first through-hole and the second through-hole.

* * * * *